(12) United States Patent
Hébert et al.

(10) Patent No.: US 12,179,036 B2
(45) Date of Patent: Dec. 31, 2024

(54) SYSTEM AND METHOD FOR STIMULATING ALERTNESS IN A SUBJECT

(71) Applicant: 14975162 CANADA INC., Mississauga (CA)

(72) Inventors: Marc Hébert, Québec (CA); Jacques Dénommée, Québec (CA); Éric Mandjee, Québec (CA); Marc Drouin, Québec (CA)

(73) Assignee: 14975162 CANADA INC., Mississauga (CA)

( * ) Notice: Subject to any disclaimer, the term of this patent is extended or adjusted under 35 U.S.C. 154(b) by 1011 days.

(21) Appl. No.: 17/261,392

(22) PCT Filed: Jul. 19, 2019

(86) PCT No.: PCT/CA2019/050993
§ 371 (c)(1),
(2) Date: Jan. 19, 2021

(87) PCT Pub. No.: WO2020/019062
PCT Pub. Date: Jan. 30, 2020

(65) Prior Publication Data
US 2021/0260403 A1 Aug. 26, 2021

Related U.S. Application Data

(60) Provisional application No. 62/703,982, filed on Jul. 27, 2018.

(51) Int. Cl.
*A61N 5/06* (2006.01)
*A61M 21/00* (2006.01)
*G16H 10/60* (2018.01)

(52) U.S. Cl.
CPC ........... *A61N 5/0618* (2013.01); *G16H 10/60* (2018.01); *A61M 21/00* (2013.01)

(58) Field of Classification Search
CPC .......................... A61M 2205/587; H05B 47/11
See application file for complete search history.

(56) References Cited

U.S. PATENT DOCUMENTS

| 10,376,710 | B2 | 8/2019 | Hebert et al. |
| 2014/0194957 | A1* | 7/2014 | Rubinfeld ............... A61F 9/013 |
| | | | 607/90 |

(Continued)

FOREIGN PATENT DOCUMENTS

| DE | 102016203164 A1 | 12/2016 |
| DE | 102016215593 A1 | 2/2018 |

(Continued)

OTHER PUBLICATIONS

Extended European Search Report of PCT/CA2019050993, Dated Jan. 20, 2022; EP Application No. 19841984.8.

(Continued)

*Primary Examiner* — Thaddeus B Cox
(74) *Attorney, Agent, or Firm* — Hamilton, Brook, Smith & Reynolds, P.C.

(57) ABSTRACT

The present invention relates to a system for stimulating alertness in a subject within an environment exposed to an ambient light having a fluctuating ambient light illuminance. The system comprises an optical generator with a light source configured to generate a stimulating light having a stimulating light irradiance; and a driver coupled to the light source for controlling the stimulating light irradiance; an ambient light sensor configured to monitor the ambient light illuminance in real-time; and a controller operatively coupled to the optical generator and to the ambient light sensor to control the stimulating light irradiance in response to the ambient light illuminance monitored by the ambient light sensor, the controlling comprising capping the stimulating light irradiance to a maximal irradiance value based (Continued)

on the monitored ambient light illuminance. The present invention also relates to a method for stimulating alertness in a subject.

20 Claims, 10 Drawing Sheets

(56) References Cited

U.S. PATENT DOCUMENTS

| | | | |
|---|---|---|---|
| 2017/0173361 A1* | 6/2017 | Hebert | A61M 21/00 |
| 2018/0133504 A1 | 5/2018 | Malchano et al. | |
| 2018/0272932 A1* | 9/2018 | Chen | B60Q 1/1423 |
| 2020/0092971 A1* | 3/2020 | Tsubota | A61N 5/0613 |

FOREIGN PATENT DOCUMENTS

| | | |
|---|---|---|
| GB | 2519352 A | 4/2015 |
| JP | 3713815 B2 | 11/2005 |
| WO | 2015052207 | 4/2015 |
| WO | 2016145059 A1 | 9/2016 |
| WO | 2017025613 A1 | 2/2017 |
| WO | 2020019062 A1 | 1/2020 |

OTHER PUBLICATIONS

PCT International Search Report and Written Opinion for International Application No. PCT/CA2019/050993, entitled: "System and Method for Stimulating Alertness in a Subject," Date of Mailing Sep. 16, 2019.

* cited by examiner

SYSTEM AND METHOD FOR STIMULATING ALERTNESS IN A SUBJECT

PRIOR APPLICATION

This application is the U.S. National Stage of International Application No. PCT/CA2019/050993, filed Jul. 19, 2019, which designates the U.S., published in English, and claims the benefit of U.S. Provisional Application No. 62/703,982 filed Jul. 27, 2018, and entitled "SYSTEM AND METHOD FOR STIMULATING VIGILANCE IN A SUBJECT." The entire teachings of the above applications are incorporated herein by reference.

FIELD OF THE INVENTION

The present invention relates to a system and a method for stimulating alertness in a subject. More particularly, this invention relates to a system and a method for stimulating alertness in a subject within a vehicle interior, the system and the method making use of an optical generator producing a stimulating light for the biological clock of the subject.

BACKGROUND OF THE INVENTION

Some activities require a constant and strong alertness of a subject. It is particularly true for drivers of motorized vehicles, such as cars, trucks or buses, whose alertness should be kept constantly high for security reasons. It is indeed known that drowsiness is responsible for many severe traffic accidents every year.

Several solutions might exist for improving alertness of a subject while driving a motorized vehicle such as drinking stimulants such as coffee or energy drinks, lowering the temperature in the vehicle interior or listening to stimulating music. However, the efficiency of these solutions is often disputed, in particular with regards to their duration. Moreover, these solutions are not always compatible with driving safety requirements and/or are not always healthy for the subject.

It would therefore be profitable to be provided with a system and a method for efficiently stimulating alertness of a subject while driving a motorized vehicle that would be compatible with driving safety requirements.

SUMMARY OF THE INVENTION

In order to address the above and other drawbacks, and in accordance with the present invention, there is disclosed a system for stimulating alertness in a subject.

According to a general aspect of the present invention, there is provided a system for stimulating alertness in a subject within an environment exposed to an ambient light having a fluctuating ambient light illuminance. The system comprises an optical generator comprising: one or more light sources configured to collectively generate a stimulating light having a stimulating light irradiance; and a driver coupled to the one or more light sources for controlling the stimulating light irradiance. The system further comprises an ambient light sensor configured to monitor the ambient light illuminance within said environment in real-time; and a controller operatively coupled to the optical generator and to the ambient light sensor to control the stimulating light irradiance in response to the ambient light illuminance monitored by the ambient light sensor, said controlling comprising capping the stimulating light irradiance to a maximal irradiance value based on the monitored ambient light illuminance.

According to another general aspect, there is provided a system for stimulating alertness in a subject within an interior exposed to an ambient light having a fluctuating ambient light illuminance, the interior being provided with an ambient light sensor configured to monitor the ambient light illuminance within said interior in real-time. The system comprises an optical generator comprising: one or more light sources configured to collectively generate a stimulating light having a stimulating light irradiance; and a driver coupled to the one or more light sources for controlling the stimulating light irradiance. The system further comprises a controller operatively coupled to the optical generator and operatively couplable to the ambient light sensor of the interior to control the stimulating light irradiance in response to the ambient light illuminance monitored by the ambient light sensor, said controlling comprising capping the stimulating light irradiance to a maximal irradiance value based on the monitored ambient light illuminance.

According to another general aspect, there is provided a method for stimulating alertness in a subject within an environment exposed to an ambient light having a fluctuating ambient light illuminance, the method comprising: generating a stimulating light having a stimulating light irradiance; monitoring the ambient light illuminance within said environment in real-time; and controlling the stimulating light irradiance in response to the monitored ambient light illuminance, said controlling comprising capping the stimulating light irradiance to a maximal irradiance value based on the monitored ambient light illuminance.

Other possible aspect(s), object(s), embodiment(s), variant(s) and/or advantage(s) of the present invention, all being preferred and/or optional, are briefly summarized hereinbelow.

In some implementations, the controlling comprises comparing the monitored ambient light illuminance to at least one threshold; and upon the monitored ambient light illuminance crossing one of said at least one threshold, changing said maximal irradiance value.

In some implementations, the system further comprises continuing said monitoring of the ambient light illuminance for a predetermined delay upon the monitored light illuminance increasing so as to pass over one of said at least one threshold and proceeding with the changing of said maximal irradiance value only if the monitored light illuminance does not decrease so as to pass under said at least one threshold during said predetermined delay.

In some implementations, the predetermined delay is comprised between about 5 seconds and about 60 seconds.

In some implementations, the predetermined delay is about 30 seconds.

In some implementations, the controlling comprises changing said maximal irradiance value substantially instantly upon the monitored light illuminance decreasing so as to pass under one of said at least one threshold.

In some implementations, the controller is operable in a plurality of modes, comprising: a Night mode having an associated Night maximal irradiance value; a Twilight mode having an associated Twilight maximal irradiance value, said Twilight maximal irradiance value being greater than the Night maximal irradiance value; a Day mode having an associated Day maximal irradiance value, said Day maximal irradiance value being greater than the Twilight maximal irradiance value. The Night mode is active when the monitored ambient light illuminance is under a Twilight Threshold; the Day mode is active when the monitored ambient light illuminance is above a Day Threshold, an illuminance value of the Day Threshold being greater than an illuminance value of the Twilight Threshold; and the Twilight mode is active when the monitored ambient light illuminance is between the Twilight Threshold and the Day Threshold.

In some implementations, the Night mode is active when the monitored ambient light illuminance increases so as to pass over a Night Threshold and is below the Twilight Threshold, an illuminance value of the Twilight Threshold being greater than the illuminance value of the Night Threshold.

In some implementations, the Twilight Mode is active when the monitored ambient light illuminance further increases so as to pass over the Twilight Threshold and is below the Day Threshold.

In some implementations, the controlling comprises continuing said monitoring of the ambient light illuminance for a predetermined delay upon the monitored light illuminance increasing so as to pass over one of the Twilight Threshold and the Day Threshold and proceeding with the corresponding changing from the Night mode to the Twilight mode and from the Twilight mode to the Day mode only if the monitored light illuminance does not decrease under said one of the Twilight Threshold and the Day Threshold during said predetermined delay.

In some implementations, the Twilight Mode is active when the monitored ambient light illuminance decreases so as to pass under the Day Threshold and is above the Twilight Threshold.

In some implementations, upon decrease of the monitored ambient light illuminance under one of the Day Threshold and the Twilight Threshold, the controlling comprises proceeding with the corresponding changing from the Day mode to the Twilight Mode and from the Twilight Mode to the Night Mode substantially instantly.

In some implementations, the Twilight maximal irradiance value represents between about 95% and about 55% of the Day maximal irradiance value.

In some implementations, the Twilight maximal irradiance value represents about 75% of the Day maximal irradiance value.

In some implementations, the Night maximal irradiance value represents between about 20% and about 50% of the Day maximal irradiance value.

In some implementations, the Night maximal irradiance value represents about 35% of the Day maximal irradiance value.

In some implementations, the controller is operated in the Night mode when the monitored ambient light illuminance is comprised between about 0 lux and about 25 lux.

In some implementations, the controller is operated in the Twilight mode when the monitored ambient light illuminance is comprised between about 25 lux and about 100 lux.

In some implementations, the controller is operated in the Day mode when the monitored ambient light illuminance is greater than or equal to about 100 lux.

In some implementations, the stimulating light has an optical parameter selected to optimize the stimulation of the suprachiasmatic nuclei (SCN) in the subject.

In some implementations, the stimulating light has a spectral profile with wavelengths ranging from about 420 nm to about 540 nm.

In some implementations, the spectral profile has wavelengths between about 446 nm and about 483 nm.

In some implementations, the optical generator is configured to generate the stimulating light in a pulsed regime having a pulsing frequency of about 60 Hz.

In some implementations, the optical generator is configured to actuate cyclically said one or more light sources, each cycle having a duration comprised between about 10 ms and about 20 ms.

In some implementations, the controller is further operable to perform an activation routine upon activation of said system, the activation routine comprising setting the stimulating light irradiance to a minimum value, and gradually increasing said stimulating light irradiance to a minimal effective value over an activation period.

In some implementations, the minimum value represents about 15% of the maximal irradiance value.

In some implementations, the activation period is comprised between about 5 minutes and about 20 minutes.

In some implementations, the activation period is comprised between about 7 minutes and about 14 minutes.

In some implementations, the system further comprises a user control device operable to vary the stimulating light irradiance within a finite range defined by a minimal effective value and a maximal operated value.

In some implementations, the minimal effective value is determined based on a minimal biologically effective irradiance known to stimulate said alertness.

In some implementations, the minimal effective value represents about 30% of the maximal irradiance value.

In some implementations, the maximal operated value is smaller than the maximal irradiance value.

In some implementations, the maximal operated value represents about 70% of the maximal irradiance value.

In some implementations, the method further comprises comparing the monitored ambient light illuminance to at least one threshold; and upon the monitored ambient light illuminance crossing one of said at least one threshold, changing said maximal irradiance value.

In some implementations, the method further comprises measuring a setting ambient light illuminance prior to the generation of the stimulating light; and determining a value of said at least one threshold as a function of the measured setting ambient light illuminance.

In some implementations, the method further comprises continuing said monitoring of the ambient light illuminance for a predetermined delay upon the monitored light intensity increasing so as to pass over one of said at least one threshold and proceeding with the changing of said maximal irradiance value only if the monitored light illuminance does not decrease so as to pass under said at least one threshold during said predetermined delay.

In some implementations, the method controlling comprises changing said maximal irradiance value substantially instantly upon the monitored light illuminance decreasing so as to pass under one of said at least one threshold.

In some implementations, the method comprises generating the stimulating light in a plurality of modes, comprising: a Night mode having an associated Night maximal irradiance value; a Twilight mode having an associated Twilight maximal irradiance value, said Twilight maximal irradiance value being greater than the Night maximal irradiance value; a Day mode having an associated Day maximal irradiance value, said Day maximal irradiance value being greater than the Twilight maximal irradiance value; wherein the Night mode is active when the monitored ambient light illuminance is under a Twilight Threshold; the Day mode is active when the monitored ambient light illuminance is above a Day Threshold, an illuminance value of the Day Threshold being greater than an illuminance value of the Twilight Threshold; and wherein the Twilight mode is active when the monitored ambient light illuminance is between the Twilight Threshold and the Day Threshold.

In some implementations, the Night mode is active when the monitored ambient light illuminance increases so as to pass over a Night Threshold and is below the Twilight Threshold, an illuminance value of the Twilight Threshold being greater than the illuminance value of the Night Threshold.

In some implementations, the Twilight Mode is active when the monitored ambient light illuminance further increases so as to pass over the Twilight Threshold and is below the Day Threshold.

In some implementations, the controlling comprises continuing said monitoring of the ambient light illuminance for a predetermined delay upon the monitored light illuminance increasing so as to pass over one of the Twilight Threshold and the Day Threshold and proceeding with the corresponding changing from the Night mode to the Twilight mode and from the Twilight mode to the Day mode only if the monitored light illuminance does not decrease under said one of the Twilight Threshold and the Day Threshold during said predetermined delay.

In some implementations, the Twilight Mode is active when the monitored ambient light illuminance decreases so as to pass under the Day Threshold and is above the Twilight Threshold.

In some implementations, upon decrease of the monitored ambient light illuminance under one of the Day Threshold and the Twilight Threshold, the controlling comprises proceeding with the corresponding changing from the Day mode to the Twilight Mode and from the Twilight Mode to the Night Mode substantially instantly.

In some implementations, the stimulating light is generated in the Night mode when the monitored ambient light illuminance is comprised between about 0 lux and about 25 lux.

In some implementations, the stimulating light is generated in the Twilight mode when the monitored ambient light illuminance is comprised between about 25 lux and about 100 lux.

In some implementations, the stimulating light is generated in the Day mode when the monitored ambient light illuminance is greater than or equal to about 100 lux.

In some implementations, generating the stimulating light further comprises performing an activation routine, the activation routine comprising setting the stimulating light irradiance to a minimum value, and gradually increasing said stimulating light irradiance to a minimal effective value over an activation period.

In some implementations, the method further comprises manually varying the stimulating light irradiance within a finite range defined by a minimal effective value and a maximal operated value.

In some implementations, the method further comprises adjusting the maximal irradiance value as a function of dimensions of the environment.

In some implementations, the maximal irradiance value is adjusted as a function of a distance between the subject and a light source of the stimulating light.

According to another embodiment of the present invention, a system for stimulating vigilance in a subject within an environment exposed to an ambient light having a fluctuating ambient light intensity (or ambient light illuminance) is provided. The system comprises an optical generator comprising one or more light sources configured to collectively generate a stimulating light having a stimulating light irradiance and a driver coupled to the one or more light sources for controlling the stimulating light irradiance. The system further comprises an ambient light sensor configured to monitor the ambient light intensity (or ambient light illuminance) within the environment in real-time, and a controller operatively coupled to the optical generator and to the ambient light sensor to control the stimulating light irradiance in response to the ambient light intensity (or ambient light illuminance) monitored by the ambient light sensor. The controlling comprises capping the stimulating light irradiance to a maximum value based on the monitored ambient light illuminance.

In one feature, the controlling comprises comparing the monitored ambient light illuminance to at least one threshold, and upon the monitored ambient light illuminance crossing one of the at least one threshold, changing the maximum value.

In another feature, the system further comprises continuing the monitoring for a predetermined delay upon the monitored light illuminance crossing one of the at least one threshold and proceeding with the changing of the maximum value only if the monitored light illuminance does not cross again the at least one threshold during the predetermined delay.

In yet another feature, the predetermined delay is about 30 seconds.

In yet another feature, the controller is operable in a plurality of modes:
  a Night mode active when the monitored ambient light illuminance is under a Night Threshold; the Night mode has an associated Night maximal irradiance value;
  a Twilight mode active when the monitored ambient light illuminance is between the Night threshold and a Day threshold; the Twilight mode has an associated Twilight maximal irradiance value and the Twilight maximal irradiance value is greater than the Night maximal irradiance value; and
  a Day mode active when the monitored ambient light illuminance is above the Day threshold; the Day mode has an associated Day maximal irradiance value and the Day maximal irradiance value is greater than the Twilight maximal irradiance value.

In one feature, the controller is further operable to perform an activation routine upon activation of the system. The activation routine comprises setting the stimulating light irradiance to a minimum value, and gradually increasing the stimulating light irradiance to a minimal effective value over an activation period.

In yet another feature, the system further comprises a user control device operable to vary the stimulating light irradiance within a finite range defined by a minimal value and the maximal value from the controller.

In yet another feature, the minimal value is determined based on a minimal biologically effective irradiance known to stimulate the vigilance.

According to another embodiment of the present invention, there is provided a method for stimulating vigilance in a subject within an environment exposed to an ambient light having a fluctuating ambient light illuminance. The method comprises generating a stimulating light having a stimulating light irradiance and monitoring the ambient light illuminance within the environment in real-time. The method further comprises controlling the stimulating light irradiance in response to the monitored ambient light illuminance; the controlling comprises capping the stimulating light irradiance to a maximum value based on the monitored ambient light illuminance.

Other objects, advantages and features of the present invention will become more apparent upon reading of the following non-restrictive description of illustrative embodiments thereof, given by way of example only with reference to the accompanying drawings.

BRIEF DESCRIPTION OF THE DRAWINGS

Having thus generally described the nature of the invention, reference will now be made to the accompanying drawings, showing by way of illustration an illustrative embodiment thereof, and in which.

DESCRIPTION OF THE ILLUSTRATIVE EMBODIMENTS

Figure 1:
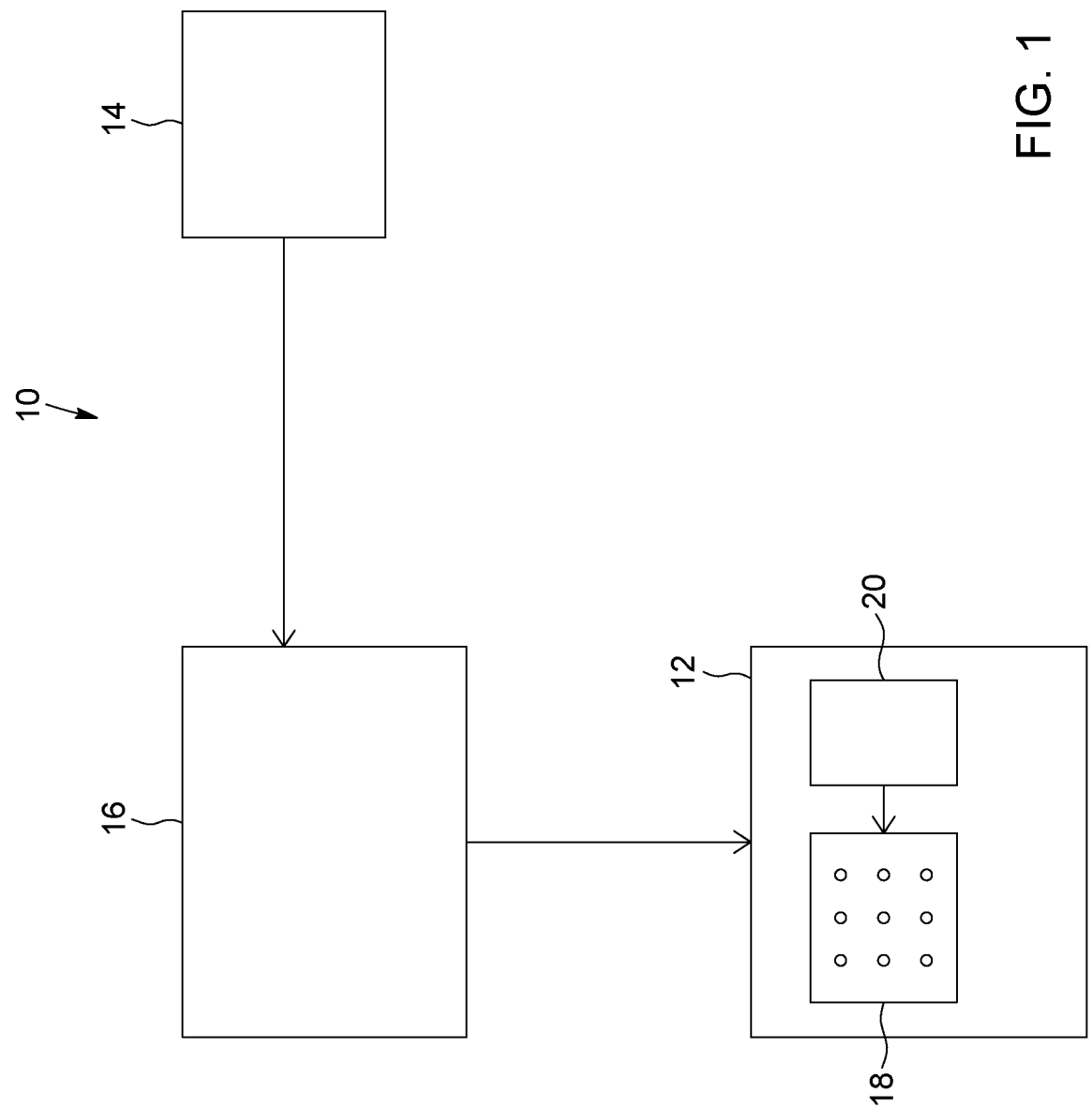
FIG. 1 is a schematic representation of a system according to one embodiment of the present invention.

The description which follows, and the embodiments described therein are provided by way of illustration of an example, or examples of particular embodiments of principles and aspects of the present invention. These examples are provided for the purpose of explanation and not of limitation, of those principles of the invention. In the description that follows, like parts are marked throughout the specification and the drawings with the same respective reference numerals.

In the following description, the term "illuminance" usually refers to the luminous flux incident on a surface, the luminous flux being emitted by light sources, either natural or artificial. In other words, the illuminance corresponds to the amount of light incident on a surface of a particular area and is for example expressed in lux (i.e. lumen per square meter). The term "intensity" is used herein according to the physics definition of power transferred per unit area, and usually refers to the light as it is received by a user or by a sensor. For instance, in the following description, the terms "intensity" and "illuminance" might refer to an ambient light of an environment. In the following description, the term "irradiance" might refer to the radiant flux (or power) received by a surface per unit area, the radiant flux being emitted for instance by the light sources of the system according to the present disclosure. For instance, the irradiance is expressed in watt per square meter.

With reference to FIG. 1, a system identified by reference numeral 10 is provided. The system 10 is configured for stimulating vigilance or alertness in a subject within an environment exposed to an ambient light having a fluctuating ambient light intensity. In the following description, the terms vigilance and alertness are used indistinctly to refer to a state of the subject being substantially constantly attentive and responsive to signs of opportunity, activity, or danger. The system 10 according to the present disclosure is configured to have an impact on the biological clock of the subject.

For instance and without being limitative, the environment is defined within a motorized vehicle interior. The vehicle may be a car, a sport utility vehicle (or SUV), a truck or a bus. The subject may be within a cab of the motorized vehicle as a driver or as a passenger.

Still referring to FIG. 1, the system 10 comprises an optical generator 12, an ambient light sensor 14 (for instance and without being limitative, one, in the embodiment shown) configured to monitor the ambient light intensity within the environment in real-time, and a controller 16 operatively coupled to the optical generator 12 and to the ambient light sensor 14.

Figure 2:
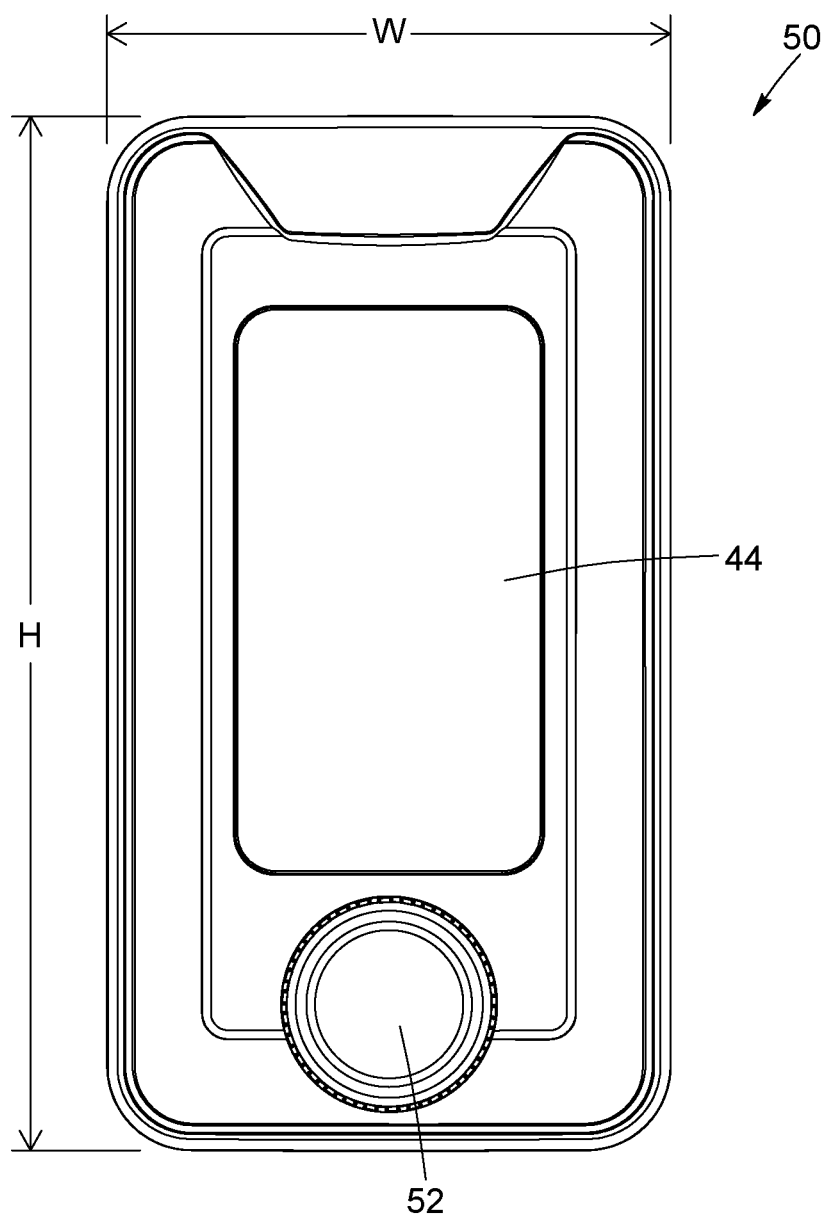
FIG. 2 is a front elevational view of a casing of the system of FIG. 1.
Figure 3:
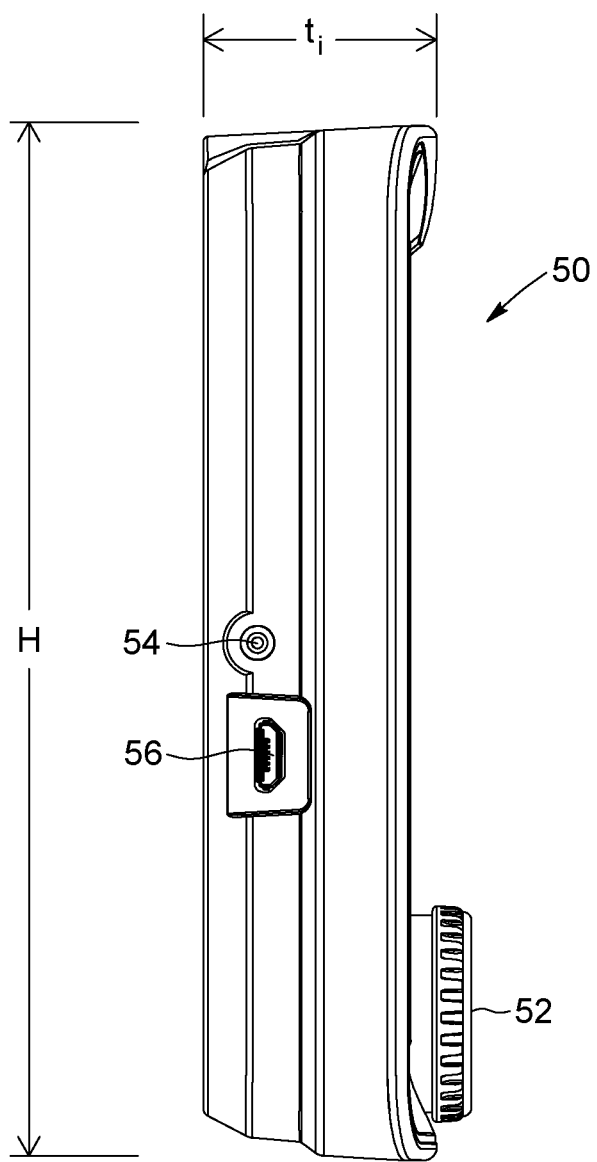
FIG. 3 is a side elevational view of the casing of FIG. 2.

As represented in FIGS. 2 and 3, the system 10 further comprises a casing 50 in which at least the optical generator 12 and the controller 16 are arranged.

In the shown embodiment, the casing 50 has a substantially parallelepipedal shape and has a height H comprised between about 7 cm and about 20 cm, a width W comprised between about 4 cm and about 10 cm and a thickness ti comprised between about 1 cm and about 4 cm. In other words, the casing 50 of the system 10 is dimensioned to be easily stored, for instance in a glove box of the vehicle. The casing 50 further comprises securing means (not represented), such as a suction cup, supports or adhesives, for the casing 50 to be easily secured in the vehicle, for instance to a portion of a wind shield of the vehicle. The casing 50 further comprises a control knob 52 configured, for instance and without being limitative, to be rotated and/or pressed; the function of the control knob 52 will be best described below. Moreover, the casing 50 can be electrically connected to an outer electrical source via an electrical connector 54 and may also be configured to exchange data with other electrical devices, for instance via a USB port 56.

Figure 4A:
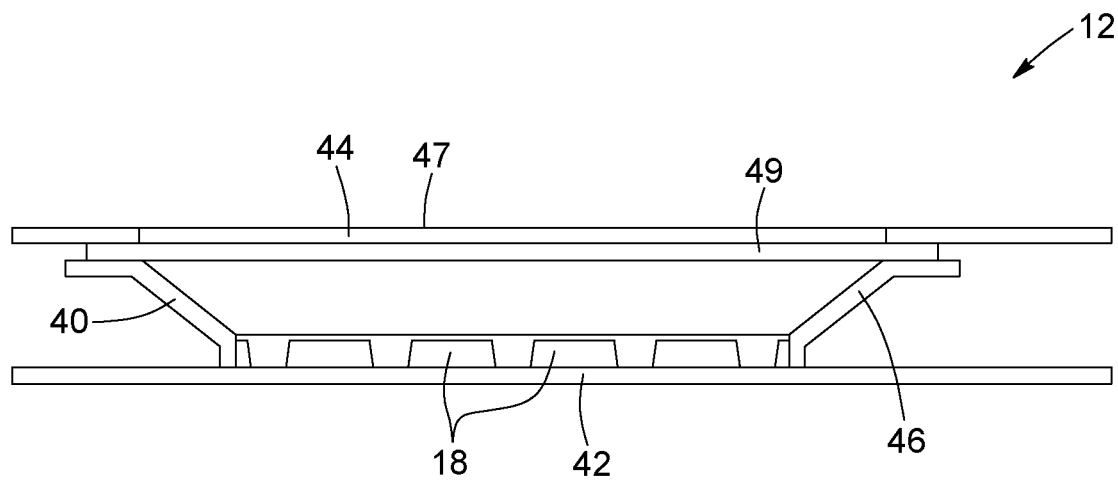
FIG. 4A is a schematic representation of a cross-section view of a housing of an optical generator of the system of FIG. 1.
Figure 4B:
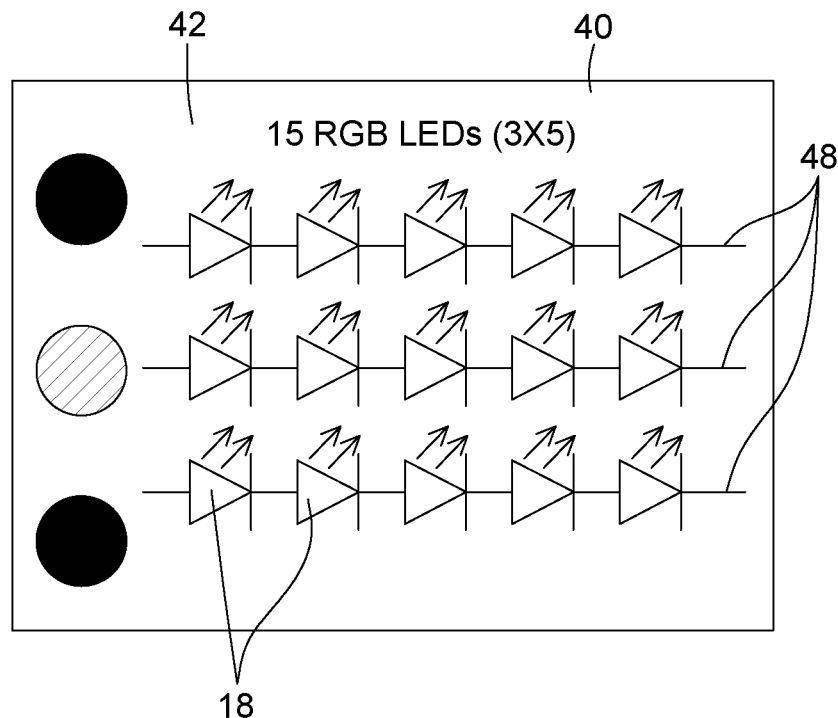
FIG. 4B is a schematic representation of a top view of the housing of FIG. 4A.

With reference to FIGS. 1, 4A and 4B, the optical generator 12 is electrically connected to an electricity source (not represented), such as a rechargeable battery, and comprises one or more light sources 18 configured to collectively generate a stimulating light having a stimulating light irradiance, and a driver 20 coupled to the one or more light sources 18 for controlling the stimulating light irradiance. In the following description, the term controlling should be understood in the sense of varying, modifying, adjusting, modulating or changing any of the parameters of the stimulating light.

The one or more light sources 18 can comprise a plurality of red, green and/or blue LEDs. According to the embodiment represented in FIG. 4A, the optical generator 12 comprises a housing 40 having a bottom wall 42, a top wall 44 and a peripheral wall 46 extending between the bottom wall 42 and the top wall 44. The LEDs are mounted to an inner face of the bottom wall 42 and define, for instance, several lines and rows. In the example represented in FIG. 4B, the optical generator 12 comprises 15 LEDs, defining 3 substantially parallel lines 48, each line comprising 5 LEDs of a same colour. It is appreciated that the number, the colors and the arrangement of the LEDs can vary from the embodiment shown. In the shown embodiment, a sheet of white paper is secured to at least one of the inner faces of the bottom wall 42 and the peripheral wall 46 so as to increase the diffusion of the stimulating light emitted by the light sources. Moreover, an Enhanced Specular Reflector film (ESR film) can further be arranged on some of the inner faces of the housing 40. A prismatic film 49 or any other optical diffuser assembly can be arranged in the optical generator 12 to increase, in particular, the uniformity of the stimulating light emitted by the light sources. The top wall 44 is formed in a material having transparency properties for the stimulating light generated by the light sources to be diffused outside the housing 40. A Brightness Enhancement Film (BEF) 47 can further be disposed on the top wall 44. It is thus understood that the housing 40 is configured to enable a substantially uniform light diffusion of the stimulating light as well as to control the angle of diffusion of the stimulating light; in the embodiment shown, the substantially uniform light diffusion is in particular enabled by the above-mentioned films 47, 49.

Research in the field of cognitive neuroscience has shown a correlation between exposure of the eyes of subjects to light having certain optical parameters and the stimulation of vigilance or alertness. In particular, it has been shown that in some circumstances, exposing the eyes of a subject to suitable light stimulation can reduce the secretion of melatonin in this subject.

Melatonin is a hormone secreted by the pineal gland, a gland under the control of the biological clock located in the suprachiasmatic nuclei (SCN). This secretion occurs mainly at night, when light conditions are low. Because melatonin has a mild sleepiness-inducing effect, its secretion is generally associated with a decrease in productivity of night-shift workers and an increase of work-related accidents, especially in a vehicle driving context. The transmission of light stimuli to the SCN is believed to be accomplished by the melanopsins, photoreceptors found in less than 1% of the total ganglion cell population. When the melanopsins of the retina are exposed to light, the SCN react by inducing pineal gland to stop melatonin secretion. Inhibition of melatonin secretion is dependent upon the efficacy of the response of SCN to light stimulus. In other words, inhibition of melatonin secretion will be stronger in the presence of a strong response of SCN to a light stimulus while inhibition of melatonin secretion is expected to be weaker in the presence of a weak response of SCN to a light stimulus. Such a response of the SCN is known to be influenced by the wavelength of the light stimulus.

In some implementations, the stimulating light may have optical parameter selected to optimize the stimulation of the suprachiasmatic nuclei (SCN) in a subject, for example based on results from neuroscience research. The spectral profile of the stimulating light can be one factor of interest. For example, there are indications that sensitivity of melanopsins is confined to a light spectrum in which wavelengths range from about 420 nm to about 540 nm, with a sensitivity or wavelength peak between about 446 nm and about 483 mm. This wavelength range encompasses the light that is generally perceived as being blue (wavelength peak at about 470 nm) and green (wavelength peak at 525 nm). Blue light has been shown to be more efficient than white light with respect to the biological impact on performance, alertness and general resynchronization of the biological clock. However, the use of blue light to modulate SCN response is not without limitation. For example, melanopsin photoreceptors tend to degrade fast and not to regenerate upon continuous exposure to blue light, which contribute to reduce the efficacy of blue light upon such sustained exposure. It can furthermore be advantageous to combine the blue light with light in other wavelength ranges. For example, in some instances exposure to red light be conducive to the regeneration of the melanopsins.

Intensity of the stimulating light is another parameter which is known to impact the stimulating effect of the exposure. For example, in the shown embodiment the different LEDs are dimensioned and configured to emit a light having an intensity sufficient so that an irradiance comprised between about 1 $\mu W/cm^2$ and about 15 $\mu W/cm^2$ for each generated color can be received by the retina of the user. In the following description, the values of the stimulating light irradiance are expressed for a distance between the retina of the user and the optical generator 12 of the order of about 1 m.

In some variants, the stimulating light may be generated in a pulsed regime. Indeed, data from the inventor's research indicates that pulsing frequency can be a factor in the stimulation of SCN. For example, one or more of the LEDs can be pulses at a pulsing frequency in the range of about 60 Hz. In other examples, the pulsing frequency can be greater or lower. Preferably, the pulsing frequency is high enough to avoid a stroboscopic effect which could bother the subject. Stroboscopic effects can be perceived around a pulsing frequency of about 50 Hz or lower.

Figure 6:
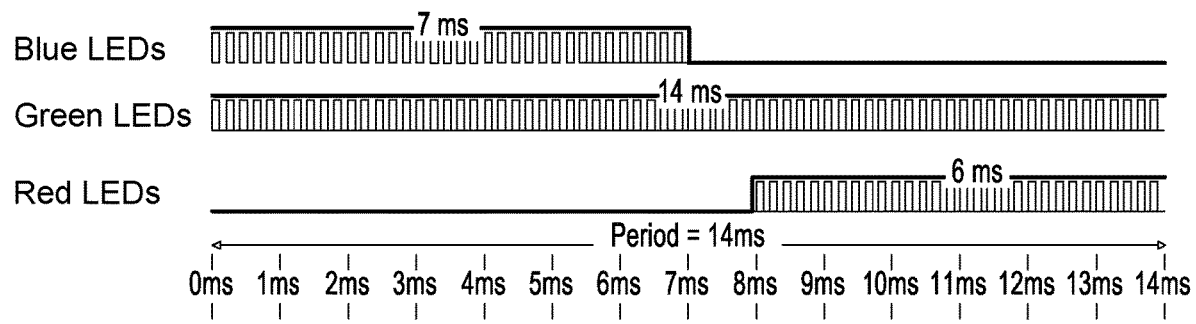
FIGS. 6 and 7 are examples of activation cycles of LEDs of an optical generator of the system, respectively in a Day mode and in a Night mode.
Figure 7:
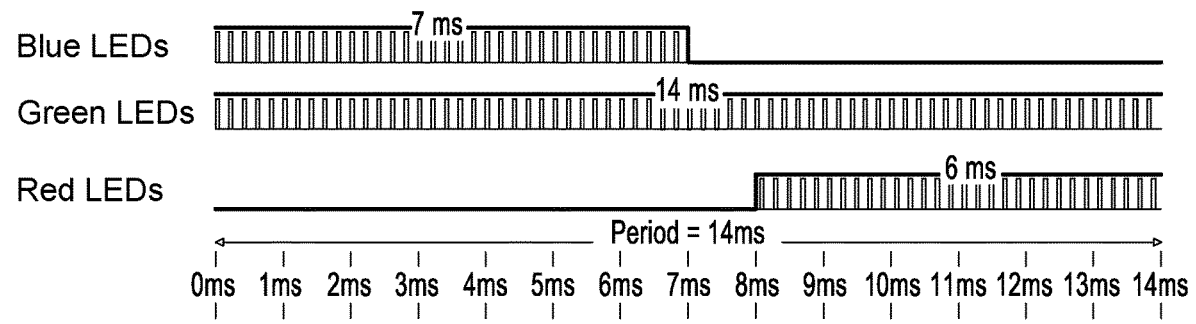

As represented in particular in FIGS. 6 and 7, the different LEDs of the optical generator 12 can be actuated simultaneously and/or successively. In some implementations, the driver 20 of the optical generator 12 is configured to actuate the different LEDs cyclically, each cycle having a duration comprised between about 10 ms and about 20 ms. In the shown embodiment in FIGS. 6 and 7, each cycle has a duration of about 14 ms. For each cycle, each LED can be either in an OFF-mode, in which no power is supplied to the LED, and an ON-mode, in which a power is provided to the LED for the LED to emit light pulses. As represented in FIGS. 6 and 7, the cycle can either start or finish with an OFF-mode period; the OFF-mode period can represent between 0% and 100% of the total period of the cycle. In some embodiments, the OFF-mode period can represent between 0% and 90% of the total period of the cycle. The driver 20 of the optical generator 12 is further configured to control the intensity of the light generated by the different LEDs, for instance via a technique of Pulse Width Modulation. Moreover, it could also be conceived embodiments in which only some of the LEDs would be actuated. For instance, in some embodiments, the driver 20 of the optical generator 12 could be configured to only actuate red and blue LEDs (i.e. in some embodiments, the OFF-mode period of the green LEDs might represent about 100% of the total period of the cycle).

As represented in FIGS. 2 and 3, the housing 40 is mounted within the casing 50 such that the stimulating light can be directed towards the subject. It is understood that the top wall 44 of the housing 40 is surrounded by a portion of a wall of the casing 50.

The ambient light sensor 14 is either mounted to the casing 50, or is apart from the casing 50, for it to be mounted in a different location of the vehicle. It could also be conceived a system 10 configured to cooperate with one of the ambient light sensors equipping the vehicle for other purposes than the one of the present invention. For instance, such ambient light sensors might be found in some vehicles to control the activation of the lighting of the vehicle. It is appreciated that the number and the location, with respect to the casing 50 or to any other place of the vehicle, of the ambient light sensors 14 can vary from the embodiment shown.

The controller 16 of the system 10 is configured to control the stimulating light irradiance generated by the light sources of the optical generator 12 in response to the ambient light intensity (or ambient light illuminance) monitored by the ambient light sensor 14. It is understood that in an embodiment of the system 10 comprising a plurality of ambient light sensors 14, the controller 16 might be configured to control independently each one of the plurality of ambient light sensors 14.

In the shown embodiment, the controller 16 is configured to cap the stimulating light irradiance to a maximum value (or maximal irradiance value) based on the monitored ambient light illuminance. It is thus understood that the controller 16 is configured to limit the risk for the subject to be dazzled by the stimulating light generated by the optical generator 12. In other words, the controller 16 is configured to limit the difference between the stimulating light irradiance and the ambient light illuminance.

In the present embodiment, and as it will be further described with reference to FIG. 5, the controller 16 is operable in at least three different modes:
- a Night mode having a Night Threshold NT and an associated Night maximal irradiance value NMV;
- a Twilight mode having a Twilight Threshold TT and an associated Twilight maximal irradiance value TMV; and
- a Day mode having a Day Threshold DT and an associated Day maximal irradiance value DMV.

In the present embodiment, the Night Threshold NT is smaller than the Twilight Threshold TT, and the Twilight Threshold TT is smaller than the Day Threshold DT. Moreover, the Night maximal irradiance value NMV is smaller than the Twilight maximal irradiance value TMV, and the Twilight maximal irradiance value TMV is smaller than the Day maximal irradiance value DMV.

In some embodiments, the Day threshold corresponds to an ambient light illuminance of the order of about 100 lux. In some embodiments, the Twilight threshold corresponds to an ambient light illuminance of the order of about 25 lux. In other words, in some embodiments, the controller 16 of the system 10 is configurable into the Day mode when the ambient light illuminance is equal to or greater than about 100 lux. In some embodiments, the controller 16 of the system 10 is configurable into the Twilight mode when the ambient light illuminance is equal to or greater than about 25 lux and is smaller than about 100 lux. In some embodiments, the controller 16 of the system 10 is configurable into the Night mode when the ambient light illuminance is greater than about 0 lux and is smaller than about 25 lux. In some embodiments, in the Day mode, the optical generator 12 is coupled with the driver 20 of the optical generator 12 for the red LEDs to generate a light having a maximum irradiance (considered as the radiant power received by a surface per unit area) comprised between about 4 $\mu W/cm^2$ and about 6 $\mu W/cm^2$ (for instance of about 5 $\mu W/cm^2$), for the green LEDs to generate a light having a maximum irradiance comprised between about 4 $\mu W/cm^2$ and about 6 $\mu W/cm^2$ (for instance of about 5 $\mu W/cm^2$) and for the blue LEDs to generate a light having a maximum irradiance comprised between about 13 $\mu W/cm^2$ and about 17 $\mu W/cm^2$ (for instance of about 15 $\mu W/cm^2$).

In some embodiments, when in the Twilight mode, the stimulating light irradiance represents between about 95% and about 55% of the stimulating light irradiance in the Day mode. In some other embodiments, when in the Twilight mode, the stimulating light irradiance represents between about 80% and about 70% of the stimulating light irradiance in the Day mode. In some other embodiments, when in the Twilight mode, the stimulating light irradiance represents about 75% of the stimulating light irradiance in the Day mode.

In some embodiments, in the Twilight mode, the optical generator 12 is coupled with the driver 20 of the optical generator 12 for the red LEDs to generate a light having a maximum irradiance (considered as the radiant power received by a surface per unit area) comprised between about 3 $\mu W/cm^2$ and about 4 $\mu W/cm^2$ (for instance of about 3.5 $\mu W/cm^2$), for the green LEDs to generate a light having a maximum irradiance comprised between about 3 $\mu W/cm^2$ and about 4 $\mu W/cm^2$ (for instance of about 3.5 $\mu W/cm^2$) and for the blue LEDs to generate a light having a maximum irradiance comprised between about 8 $\mu W/cm^2$ and about 12 $\mu W/cm^2$ (for instance of about 10 $\mu W/cm^2$).

In some embodiments, when in the Night mode, the stimulating light irradiance represents between about 20% and about 50% of the stimulating light irradiance in the Day mode. In some other embodiments, when in the Night mode, the stimulating light irradiance represents between about 25% and about 45% of the stimulating light irradiance in the Day mode. In some other embodiments, when in the Night mode, the stimulating light irradiance represents between about 30% and about 40% of the stimulating light irradiance in the Day mode. In yet some other embodiments, when in the Night mode, the stimulating light irradiance represents about 35% of the stimulating light irradiance in the Day mode.

In some embodiments, in the Night mode, the optical generator 12 is coupled with the driver 20 of the optical generator 12 for the red LEDs to generate a light having a maximum irradiance (considered as the radiant power received by a surface per unit area) comprised between about 1 $\mu W/cm^2$ and about 2 $\mu W/cm^2$ (for instance of about 1.5 $\mu W/cm^2$), for the green LEDs to generate a light having a maximum irradiance comprised between about 1 $\mu W/cm^2$ and about 2 $\mu W/cm^2$ (for instance of about 1.5 $\mu W/cm^2$) and for the blue LEDs to generate a light having a maximum irradiance comprised between about 3 $\mu W/cm^2$ and about 5 $\mu W/cm^2$ (for instance of about 4 $\mu W/cm^2$).

The present disclosure is obviously not limited to the mentioned values of the illuminance corresponding to the different thresholds. Moreover, the present disclosure is obviously not limited to a controller operable in three different modes. For instance, it could be conceived a system having a controller that would be operable in at least a fourth mode. For instance and without being limitative, the controller could be operable in a Darkness mode having a Darkness Threshold and an associated Darkness maximal irradiance value. The Darkness Threshold would be smaller than the Night Threshold NT and the Darkness maximal irradiance value would be smaller than the Night maximal irradiance value NMV. In some embodiments, when in the Darkness mode, the stimulating light irradiance represents between about 10% and about 30% of the stimulating light irradiance in the Day mode. In some other embodiments, when in the Darkness mode, the stimulating light irradiance represents between about 15% and about 25% of the stimulating light irradiance in the Day mode. In some other embodiments, when in the Darkness mode, the stimulating light irradiance represents about 20% of the stimulating light irradiance in the Day mode.

The definition of at least one additional mode (or additional environmental luminous intensity mode) having lower threshold and maximal irradiance value could thus further limit any dazzling risk of the subject.

In the embodiment shown, the driver 20 comprises LUT tables that are configured to control the luminous power of the light generated by the different LEDs and to apply a conversion factor to the power supplied to each LED, as known in the art.

FIGS. 6 and 7 represent examples of cycles of light pulses when the controller 16 is respectively in the Day mode and in the Night mode. In the shown embodiment, the cycles distinguish from each other by the duration of each light pulse, so as to modify the irradiance of the stimulating light, whereas the frequency of the light pulses is unchanged between the Night and the Day modes. As mentioned above, it could be conceived other examples of cycles of light pulses in which the LEDs of at least one specific color (for instance green LEDs) would not be actuated during all the cycle. Other examples of cycles of light pulses can be conceived, for instance for the above-mentioned Darkness and Twilight modes.

Figure 5:
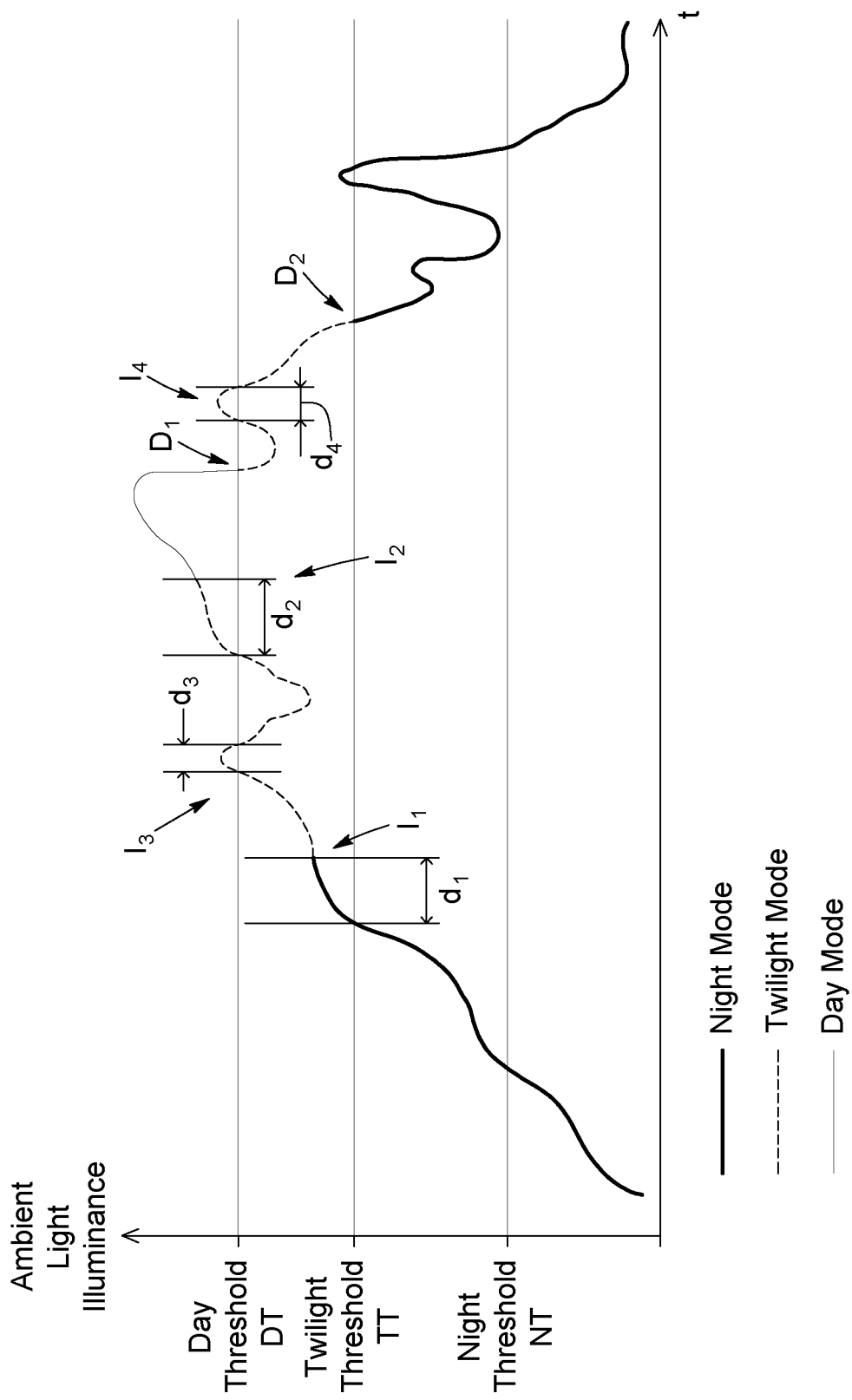
FIG. 5 is a graph illustrating the different modes of a controller of the system as a function of the evolution of the ambient light intensity.

As represented in FIG. 5, the controller 16 is configured to adapt the mode in which it operates to the value of the monitored ambient light intensity (or ambient light illuminance). When the ambient light illuminance decreases so as to pass under the Day Threshold DT, as referenced by D1 in FIG. 5, the controller 16 goes from the Day mode to the Twilight mode; when the ambient light illuminance further decreases so as to pass under the Twilight Threshold TT, as referenced by D2 in FIG. 5, the controller 16 goes from the Twilight mode to the Night mode. For safety reasons, in order to limit any dazzling risk, the controller 16 is configured to automatically and substantially instantly (i.e. without any significant delay) go from the current mode to a mode having a smaller maximal irradiance value when the ambient light illuminance decreases so as to pass under the corresponding threshold. In some embodiments, the controller 16 is configured to go from the current mode to a mode having a smaller maximal irradiance value when the ambient light illuminance decreases so as to pass under the corresponding threshold within a delay having a duration smaller than a few seconds. In some embodiments, the duration is smaller than one second. In some other embodiments, the duration is of the order of a few ms, for instance of the order of 3 ms.

The controller 16 is further configured to allow an increase of the stimulating light irradiance when the ambient light illuminance increases. When the ambient light illuminance increases so as to pass over the Twilight Threshold TT, as referenced by 11 in FIG. 5, the controller 16 goes from the Night mode to the Twilight mode; when the ambient light illuminance further increases so as to pass over the Day Threshold DT, as referenced by 12 in FIG. 5, the controller 16 goes from the Twilight mode to the Day mode.

It is thus understood that the controller 16 is configured to compare the monitored ambient light illuminance to at least one of the Night Threshold NT, the Twilight Threshold TT and the Day Threshold DT, and, upon the monitored ambient light illuminance crossing one of the thresholds, changing from a mode to another one (i.e. changing the maximal irradiance value of the stimulating light). It is understood that the expression "crossing a threshold" should be understood as referring to the fact that the monitored ambient light illuminance either increases so as to pass over the threshold or decreases so as to pass under the threshold.

The controller 16 is further configured to avoid repetitive passing from one mode to the other, when the ambient light illuminance is briefly increased, for instance due to an oncoming car having its lights on. To this end, the controller 16 is configured to compare the monitored ambient light illuminance to the corresponding threshold (i.e. to the Twilight Threshold TT when the controller 16 is in the Night mode, or to the Day Threshold DT when the controller 16 is in the Twilight mode), to continue monitoring for a predetermined delay upon the monitored light illuminance passing over the corresponding threshold and to proceed to the changing of the mode, and thus to the changing of the corresponding maximal irradiance value, only if the monitored light illuminance does not pass under the corresponding threshold during the predetermined delay. In some embodiments, the predetermined delay is comprised between about 5 seconds and about 60 seconds. In some other embodiments, the predetermined delay is comprised between about 20 seconds and about 40 seconds. In still some other embodiments, the predetermined delay is about 30 seconds.

It is thus understood that as represented in FIG. 5, the controller 16 passes respectively to the Twilight mode and to the Day mode at 11 and 12 only after a duration d1, d2 corresponding to the predetermined delay. As represented in 13, even though the ambient light illuminance increases so as to pass over the Day threshold DT, the controller 16 does not change from the Twilight mode to the Day mode, the duration d3 during which the ambient light illuminance is greater than the Day Threshold DT being smaller than the predetermined delay. Similarly, as represented in 14, even though the ambient light illuminance increases so as to pass over the Day threshold DT, the controller 16 does not change from the Twilight mode to the Day mode, the duration d4 during which the ambient light illuminance is greater than the Day Threshold DT being smaller than the predetermined delay.

Still for safety purposes, and as represented in FIG. 5, in some embodiments, when the system 10 goes from a non-powered or off state in which no stimulating light is generated, to a powered or on state, in which the optical generator 12 is actuated to generate a stimulating light, the controller 16 is initially set to the Night mode, before possible changing to the Twilight mode and to the Day mode as a function of the monitored ambient light illuminance.

Figure 8:
FIG. 8 is a graph illustrating the temporal variation of the stimulating light irradiance.

Moreover, as represented in FIG. 8, the controller 16 is further operable to perform an activation routine upon activation of the system 10 (i.e. when the system 10 passes from the off state to the on state, for instance by actuating the above-mentioned control knob 52). The activation routine comprises setting the stimulating light irradiance to a minimum value MV at which the stimulating light will not dazzle the subject, and gradually increasing the stimulating light irradiance to a minimal effective value MinV over an activation period ap. In some embodiments, the activation period ap is comprised between about 5 minutes and about 20 minutes. In some other embodiments, the activation period ap is comprised between about 7 minutes and about 14 minutes. An activation period comprised between about 7 minutes and about 14 minutes has indeed been proved to be necessary for the cones of an eye of a subject to get used to a light level change.

In some embodiments, the minimum value MV is comprised between about 5% and about 25% of the maximal irradiance value of the corresponding mode (i.e. between about 5% and about 25% of the Night maximal irradiance value NMV when the controller 16 is in the Night mode, between about 5% and about 25% of the Twilight maximal irradiance value TMV when the controller 16 is in the Twilight mode, and between about 5% and about 25% of the Day maximal irradiance value DMV when the controller 16 is in the Day mode). In some other embodiments, the minimum value MV is comprised between about 10% and about 20% of the maximal irradiance value of the corresponding mode (i.e. between about 10% and about 20% of the Night maximal irradiance value NMV when the controller 16 is in the Night mode, between about 10% and about 20% of the Twilight maximal irradiance value TMV when the controller 16 is in the Twilight mode, and between about 10% and about 20% of the Day maximal irradiance value DMV when the controller 16 is in the Day mode). In some other embodiments, the minimum value MV corresponds to about 15% of the maximal irradiance value of the corresponding mode (i.e. about 15% of the Night maximal irradiance value NMV when the controller 16 is in the Night mode, about 15% of the Twilight maximal irradiance value TMV when the controller 16 is in the Twilight mode, and about 15% of the Day maximal irradiance value DMV when the controller 16 is in the Day mode).

The system 10 further comprises a user control device, comprising for instance the above-mentioned control knob 52, that is configured, as represented in FIG. 8, to vary the stimulating light irradiance within a finite range defined by the minimal effective value MinV and a maximal operated value MaxV. In the shown embodiment, the minimal effective value MinV is determined based on a minimal biologically effective intensity known to stimulate the alertness of the subject. Thus, the subject is not allowed to decrease the stimulating light irradiance below the minimal effective value MinV determined based on the minimal biologically effective intensity. The maximal value MaxV of the range in which the subject is allowed to vary the stimulating light irradiance might be smaller than—or is determined based on—the maximal irradiance value of the corresponding mode of the controller 16.

In some embodiments, the minimal effective value MinV is comprised between about 20% and about 40% of the maximal irradiance value of the corresponding mode (i.e. between about 20% and about 40% of the Night maximal irradiance value NMV when the controller 16 is in the Night mode, between about 20% and about 40% of the Twilight maximal irradiance value TMV when the controller 16 is in the Twilight mode, and between about 20% and about 40% of the Day maximal irradiance value DMV when the controller 16 is in the Day mode). In some other embodiments, the minimal effective value MinV is comprised between about 25% and about 35% of the maximal irradiance value of the corresponding mode (i.e. between about 25% and about 35% of the Night maximal irradiance value NMV when the controller 16 is in the Night mode, between about 25% and about 35% of the Twilight maximal irradiance value TMV when the controller 16 is in the Twilight mode, and between about 25% and about 35% of the Day maximal irradiance value DMV when the controller 16 is in the Day mode). In some other embodiments, the minimal effective value MinV corresponds to about 30% of the maximal irradiance value of the corresponding mode (i.e. about 30% of the Night maximal irradiance value NMV when the controller 16 is in the Night mode, about 30% of the Twilight maximal irradiance value TMV when the controller 16 is in the Twilight mode, and about 30% of the Day maximal irradiance value DMV when the controller 16 is in the Day mode).

In some embodiments, the maximal operated value MaxV is smaller than the maximal irradiance value of the corresponding mode. In some embodiments, the maximal operated value MaxV is comprised between about 50% and about 90% of the maximal irradiance value of the corresponding mode (i.e. between about 50% and about 90% of the Night maximal irradiance value NMV when the controller 16 is in the Night mode, between about 50% and about 90% of the Twilight maximal irradiance value TMV when the controller 16 is in the Twilight mode, and between about 50% and about 90% of the Day maximal irradiance value DMV when the controller 16 is in the Day mode). In some other embodiments, the maximal operated value MaxV is comprised between about 60% and about 80% of the maximal irradiance value of the corresponding mode (i.e. between about 60% and about 80% of the Night maximal irradiance value NMV when the controller 16 is in the Night mode, between about 60% and about 80% of the Twilight maximal irradiance value TMV when the controller 16 is in the Twilight mode, and between about 60% and about 80% of the Day maximal irradiance value DMV when the controller 16 is in the Day mode). In some other embodiments, the maximal operated value MaxV corresponds to about 70% of the maximal irradiance value of the corresponding mode (i.e. about 70% of the Night maximal irradiance value NMV when the controller 16 is in the Night mode, about 70% of the Twilight maximal irradiance value TMV when the controller 16 is in the Twilight mode, and about 70% of the Day maximal irradiance value DMV when the controller 16 is in the Day mode).

It is appreciated that the respective ratio of the minimal value MV, the minimal effective value MinV and the maximal operated value MaxV with respect to the maximal irradiance value of the corresponding mode can vary from the embodiment shown.

The system 10 is further configured to take a setting configuration, in which the subject can adjust some of the parameters of the system. Indeed, it is to be noted that some parameters of the system 10 of the present disclosure depend on the environment in which it is used. For instance and without being limitative, the parameters of the stimulating light might highly depend on the distance between the subject and the system 10 (for instance the distance between the subject and the optical generator 12), on the type of the vehicle equipped with the system 10, on the dimensions of the room or space in which the subject is located, on the sensibility of the subject to a stimulating light. To this end, the system 10 may further comprise a user interface, for instance comprising the above-mentioned control knob 52 or any other adapted means, for the subject to adjust some of the parameters of the system 10.

For instance and without being limitative, different environmental dimension modes could be conceived, corresponding respectively to a distance between the subject and the system 10 smaller than about 50 cm, a distance between the subject and the system 10 being comprised between about 50 cm and about 60 cm, a distance between the subject and the system 10 being comprised between about 60 cm and about 70 cm and a distance between the subject and the system 10 being greater than about 70 cm. Different environmental dimension modes could be conceived. A different ratio could correspond to each of the different environmental dimension modes.

In some embodiments, when in the environmental dimension mode corresponding to a distance between the subject and the system 10 smaller than about 50 cm, the stimulating light irradiance represents between about 30% and about 50% of the stimulating light irradiance of the environmental dimension mode corresponding to a distance between the subject and the system 10 greater than about 70 cm. In some other embodiments, when in the environmental dimension mode corresponding to the distance between the subject and the system 10 smaller than about 50 cm, the stimulating light irradiance represents about 40% of the stimulating light irradiance of the environmental dimension mode corresponding to the distance between the subject and the system 10 greater than about 70 cm.

In some embodiments, when in the environmental dimension mode corresponding to a distance between the subject and the system 10 comprised between about 50 cm and about 60 cm, the stimulating light irradiance represents between about 55% and about 75% of the stimulating light irradiance of the environmental dimension mode corresponding to a distance between the subject and the system 10 greater than about 70 cm. In some other embodiments, when in the environmental dimension mode corresponding to the distance between the subject and the system 10 comprised between about 50 cm and about 60 cm, the stimulating light irradiance represents about 65% of the stimulating light irradiance of the environmental dimension mode corresponding to the distance between the subject and the system 10 greater than about 70 cm.

In some embodiments, when in the environmental dimension mode corresponding to a distance between the subject and the system 10 comprised between about 60 cm and about 70 cm, the stimulating light irradiance represents between about 75% and about 95% of the stimulating light irradiance of the environmental dimension mode corresponding to a distance between the subject and the system 10 greater than about 70 cm. In some other embodiments, when in the environmental dimension mode corresponding to the distance between the subject and the system 10 comprised between about 60 cm and about 70 cm, the stimulating light irradiance represents about 85% of the stimulating light irradiance of the environmental dimension mode corresponding to the distance between the subject and the system 10 greater than about 70 cm.

It is appreciated that the number of the environmental dimension modes and the ratios of the values of the stimulating light irradiance in the different environmental dimension modes can vary from the embodiment shown.

It is thus understood that the minimum value MV, the minimal effective value MinV and the maximal operated value MaxV depend for instance and without being limitative on the environmental luminous intensity mode in which the controller 16 is operated (i.e. depend on the one of the above-mentioned Darkness mode, Night mode, Twilight mode and Day mode in which the controller 16 is operated, i.e. depend on the illuminance of the ambient light). The minimum value MV, the minimal effective value MinV and the maximal operated value MaxV further depend on the environmental dimension mode that has been set.

The values of the thresholds of the different modes (i.e. the values of the Night Threshold NT, the Twilight Threshold TT and the Day Threshold DT) might need to be adjusted, for instance to take into account the dimensions of the openings or windows formed in the vehicle, the location of the ambient light sensor in the vehicle or the presence of tinted windows. To this end, the system 10 might be configured to measure an ambient light illuminance, the values of the different thresholds being then determined on the basis of the measured ambient light illuminance by the ambient light sensor.

When the system 10 is in the setting configuration, the optical generator 12 might be configured to signal (for instance via an audible or visual signal) to the subject that his/her input has been saved in the system 10, or to let him/her know about the value of one of the parameters. The optical generator 12 can further be configured to signal (for instance via an audible or visual signal) to the subject in which one of the on—or powered—state, the off—or non-powered-state or the setting configuration the system 10 currently is.

Figure 9A:
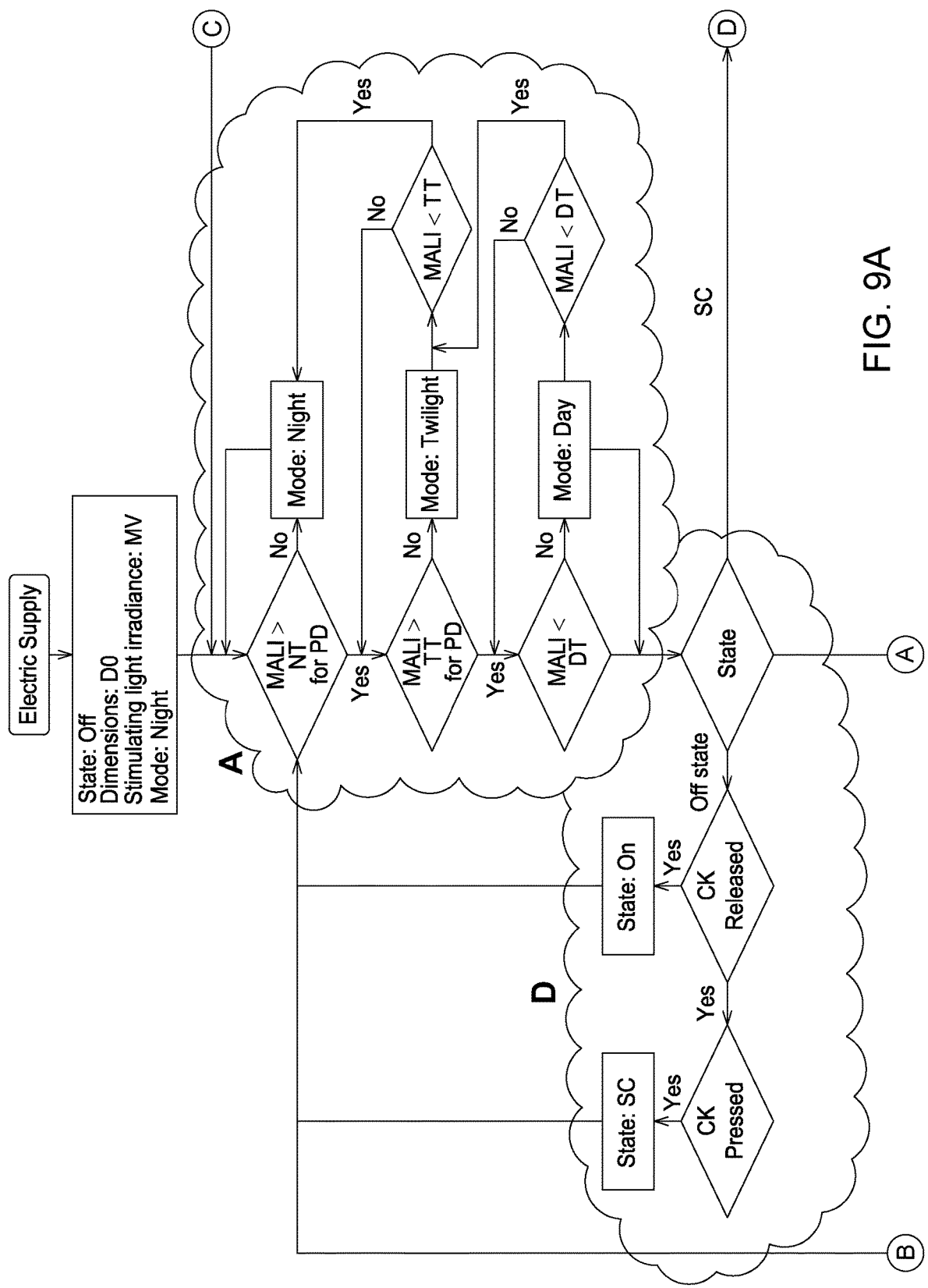
FIGS. 9A, 9B and 9C are diagrams summarizing an example of operation of the system of FIG. 1.
Figure 9B:
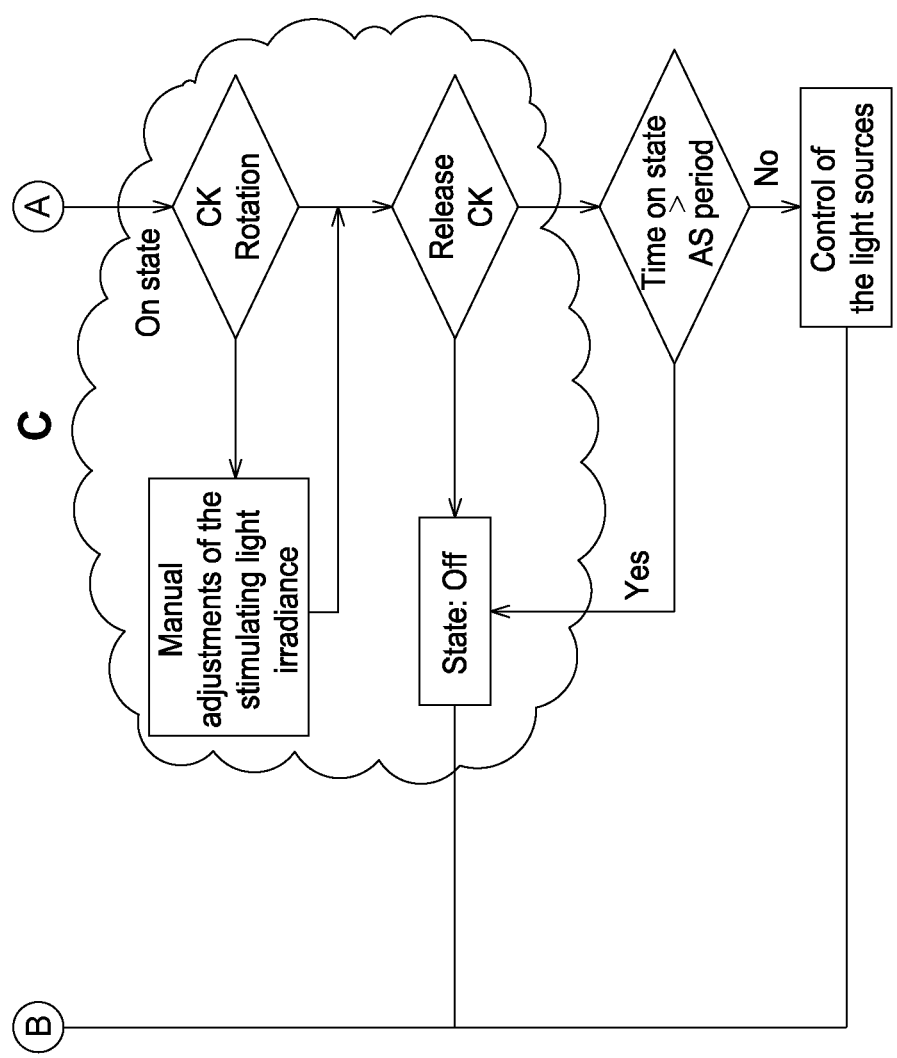
Figure 9C:
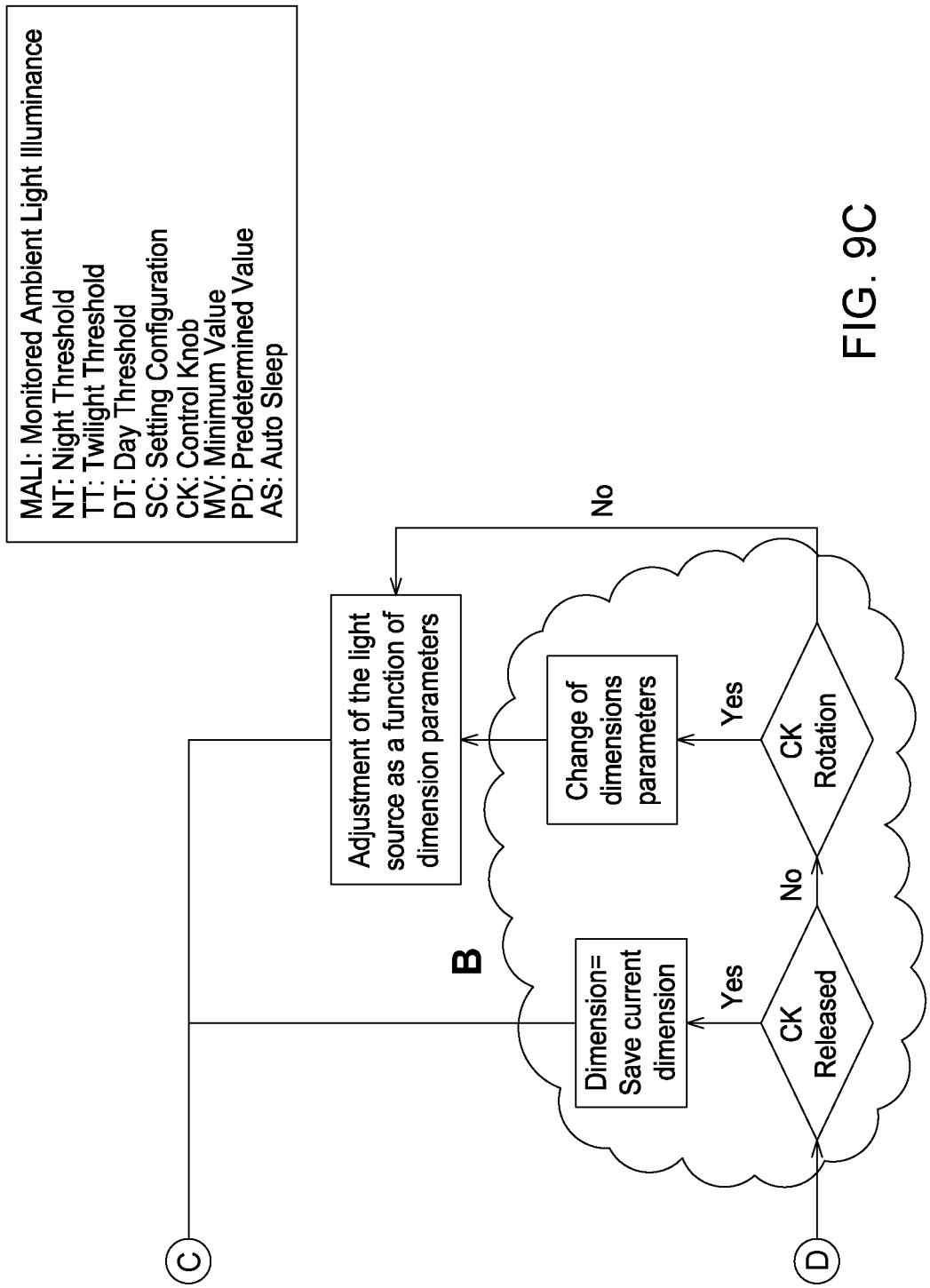

The diagrams of FIGS. 9A, 9B and 9C summarize an example of operation of the system 10:

Block A of the diagram of FIG. 9A schematically represents the control of the stimulating light irradiance by the controller 16 in response to the ambient light illuminance monitored by the ambient light sensor 14;

Block B of the diagram of FIG. 9C schematically represents the modification of one of the dimension parameters of the system 10, for instance the distance between the subject and the system 10, by the subject when the system 10 is in the setting configuration. The modification of the parameters might be realised by the actuation of the control knob 52, as represented in FIG. 9C; in some embodiments, the modification of the parameters might be realised via the above-mentioned user interface;

Block C of the diagram of FIG. 9B schematically represents the manual variation of the stimulating light irradiance by the actuation of the user control device between the minimal effective value MinV and the maximal operated value MaxV; and Block D of the diagram of FIG. 9A schematically represents the system 10 going from one of the on state, the off state or the setting configuration to another.

As represented, in the embodiment shown, the system 10 can be in the on—or powered—state, in the off—or non-powered-state, or in the setting configuration.

When in the powered state, the mode of the system 10 can either be day, twilight or night; as mentioned above, it should be noted that the system 10 is not limited to these three modes.

Moreover, the system 10 can comprise a storage system to store data relative to the use of the system 10, when in the on state. Data relative, for instance and without being limitative, to the controller 16 going from a mode to another, to the manual setting of some of the above-mentioned parameters, to the intensity of the light generated by the LEDs of the optical generator 12 can be saved; these data could further be analysed to better understand the use of the system 10 by the subject.

A person skilled in the art will appreciate that numerous system configurations would be possible for stimulate alertness in the subject. For instance, depending on the vehicle/room in which the system is to be installed, different light sources could be used.

The invention claimed is:

1. A system for stimulating alertness in a subject within an interior exposed to an ambient light having a fluctuating ambient light illuminance, the interior being provided with an ambient light sensor configured to monitor the ambient light illuminance within said interior in real-time, the system comprising:

an optical generator comprising:
one or more light sources configured to collectively generate a stimulating light having a stimulating light irradiance; and
a driver coupled to the one or more light sources for controlling the stimulating light irradiance; and a controller operatively coupled to the optical generator and operatively couplable to the ambient light sensor of the interior to control the stimulating light irradiance in response to the ambient light illuminance monitored by the ambient light sensor, said controlling comprising capping the stimulating light irradiance to a maximal irradiance value based on the monitored ambient light illuminance, the controller being operable in a plurality of modes, comprising:
a Night mode having an associated Night maximal irradiance value;
a Twilight mode having an associated Twilight maximal irradiance value, said Twilight maximal irradiance value being greater than the Night maximal irradiance value;
a Day mode having an associated Day maximal irradiance value, said Day maximal irradiance value being greater than the Twilight maximal irradiance value; wherein
the Night mode is active when the monitored ambient light illuminance is under a Twilight Threshold;
the Day mode is active when the monitored ambient light illuminance is above a Day Threshold, an illuminance value of the Day Threshold being greater than an illuminance value of the Twilight Threshold; and wherein
the Twilight mode is active when the monitored ambient light illuminance is between the Twilight Threshold and the Day Threshold;
wherein the Night mode is active when the monitored ambient light illuminance increases so as to pass over a Night Threshold and is below the Twilight Threshold, an illuminance value of the Twilight Threshold being greater than the illuminance value of the Night Threshold and wherein the Twilight mode is active when the monitored ambient light illuminance further increases so as to pass over the Twilight Threshold and is below the Day Threshold.

2. The system according to claim 1, wherein said controlling comprises:
comparing the monitored ambient light illuminance to at least one threshold;
monitoring the ambient light illuminance for a predetermined delay upon the monitored ambient light illuminance increasing so as to pass over one of said at least one threshold; and
proceeding with changing said maximal irradiance value only if the monitored ambient light illuminance does not decrease so as to pass under said at least one threshold during said predetermined delay.

3. The system according to claim 1, wherein the controlling comprises continuing said monitoring of the ambient light illuminance for a predetermined delay upon the monitored ambient light illuminance increasing so as to pass over one of the Twilight Threshold and the Day Threshold and proceeding with changing from the Night mode to the Twilight mode or from the Twilight mode to the Day mode only if the monitored ambient light illuminance does not decrease under said one of the Twilight Threshold and the Day Threshold during said predetermined delay.

4. The system according to claim 1, wherein the Twilight mode is active when the monitored ambient light illuminance decreases so as to pass under the Day Threshold and is above the Twilight Threshold and wherein, upon decrease of the monitored ambient light illuminance under one of the Day Threshold and the Twilight Threshold, the controlling comprises proceeding with changing from the Day mode to the Twilight mode or from the Twilight mode to the Night mode instantly.

5. The system according to claim 1, wherein the stimulating light has an optical parameter selected to optimize a stimulation of a suprachiasmatic nuclei (SCN) in the subject.

6. The system according to claim 1, wherein the optical generator is configured to generate the stimulating light in a pulsed regime having a pulsing frequency of about 60 Hz.

7. A method for stimulating alertness in a subject within an environment exposed to an ambient light having a fluctuating ambient light illuminance, the method comprising:
generating a stimulating light having a stimulating light irradiance;
monitoring the ambient light illuminance within said environment in real-time;
controlling the stimulating light irradiance in response to the monitored ambient light illuminance, said controlling comprising capping the stimulating light irradiance to a maximal irradiance value based on the monitored ambient light illuminance;
comparing the monitored ambient light illuminance to at least one threshold;
upon the monitored ambient light illuminance crossing one of said at least one threshold, changing said maximal irradiance value;
measuring a setting ambient light illuminance prior to the generation of the stimulating light; and
determining a value of said at least one threshold as a function of the measured setting ambient light illuminance.

8. The method according to claim 7, further comprising continuing said monitoring of the ambient light illuminance for a predetermined delay upon a monitored light intensity increasing so as to pass over one of said at least one threshold and proceeding with changing said maximal irradiance value only if the monitored ambient light illuminance does not decrease so as to pass under said at least one threshold during said predetermined delay.

9. The method according to claim 7, wherein the method comprises generating the stimulating light in a plurality of modes, comprising:
a Night mode having an associated Night maximal irradiance value;
a Twilight mode having an associated Twilight maximal irradiance value, said Twilight maximal irradiance value being greater than the Night maximal irradiance value;
a Day mode having an associated Day maximal irradiance value, said Day maximal irradiance value being greater than the Twilight maximal irradiance value; wherein
the Night mode is initially set and remains active when the monitored ambient light illuminance is under a Twilight Threshold;
the Day mode is active when the monitored ambient light illuminance is above a Day Threshold, an illuminance value of the Day Threshold being greater than an illuminance value of the Twilight Threshold; and wherein
the Twilight mode is active when the monitored ambient light illuminance is between the Twilight Threshold and the Day Threshold.

10. The method according to claim 9, wherein the Night mode is active when the monitored ambient light illuminance increases so as to pass over a Night Threshold and is below the Twilight Threshold, an illuminance value of the Twilight Threshold being greater than the illuminance value of the Night Threshold and wherein the Twilight mode is active when the monitored ambient light illuminance further increases so as to pass over the Twilight Threshold and is below the Day Threshold.

11. The method according to claim 10, wherein the Twilight mode is active when the monitored ambient light illuminance decreases so as to pass under the Day Threshold and is above the Twilight Threshold and wherein, upon decrease of the monitored ambient light illuminance under one of the Day Threshold and the Twilight Threshold, the controlling comprises proceeding with changing from the Day mode to the Twilight mode or from the Twilight mode to the Night mode substantially instantly.

12. The method according to claim 7, further comprising adjusting the maximal irradiance value as a function of at least one of dimensions of the environment and a distance between the subject and a light source of the stimulating light.

13. A system for stimulating alertness in a subject within an interior exposed to an ambient light having a fluctuating ambient light illuminance, the interior being provided with an ambient light sensor configured to monitor the ambient light illuminance within said interior in real-time, the system comprising:
an optical generator comprising:
one or more light sources configured to collectively generate a stimulating light having a stimulating light irradiance; and
a driver coupled to the one or more light sources for controlling the stimulating light irradiance; and
a controller operatively coupled to the optical generator and operatively couplable to the ambient light sensor of the interior to control the stimulating light irradiance in response to the ambient light illuminance monitored by the ambient light sensor, said controlling comprising capping the stimulating light irradiance to a maximal irradiance value based on the monitored ambient light illuminance,
wherein said controller is further operable to perform an activation routine upon activation of said system, the activation routine comprising setting the stimulating light irradiance to a minimum value, and gradually increasing said stimulating light irradiance to a minimal effective value over an activation period.

14. The system according to claim 13, wherein said controlling comprises:
comparing the monitored ambient light illuminance to at least one threshold;
monitoring the ambient light illuminance for a predetermined delay upon the monitored ambient light illuminance increasing so as to pass over one of said at least one threshold; and
proceeding with changing said maximal irradiance value only if the monitored ambient light illuminance does not decrease so as to pass under said at least one threshold during said predetermined delay.

15. The system according to claim 13, wherein the stimulating light has an optical parameter selected to optimize a stimulation of a suprachiasmatic nuclei (SCN) in the subject.

16. The system according to claim 13, wherein the optical generator is configured to generate the stimulating light in a pulsed regime having a pulsing frequency of about 60 Hz.

17. A system for stimulating alertness in a subject within an interior exposed to an ambient light having a fluctuating ambient light illuminance, the interior being provided with an ambient light sensor configured to monitor the ambient light illuminance within said interior in real-time, the system comprising:
an optical generator comprising:
one or more light sources configured to collectively generate a stimulating light having a stimulating light irradiance; and
a driver coupled to the one or more light sources for controlling the stimulating light irradiance;
a controller operatively coupled to the optical generator and operatively couplable to the ambient light sensor of the interior to control the stimulating light irradiance in response to the ambient light illuminance monitored by the ambient light sensor, said controlling comprising capping the stimulating light irradiance to a maximal irradiance value based on the monitored ambient light illuminance, and
a user control device operable to vary the stimulating light irradiance within a finite range defined by a minimal effective value and a maximal operated value and wherein said minimal effective value is determined based on a minimal biologically effective irradiance known to stimulate said alertness.

18. The system according to claim 17, wherein said controlling comprises:
comparing the monitored ambient light illuminance to at least one threshold;
monitoring the ambient light illuminance for a predetermined delay upon the monitored ambient light illuminance increasing so as to pass over one of said at least one threshold; and
proceeding with changing said maximal irradiance value only if the monitored ambient light illuminance does not decrease so as to pass under said at least one threshold during said predetermined delay.

19. The system according to claim 17, wherein the stimulating light has an optical parameter selected to optimize a stimulation of a suprachiasmatic nuclei (SCN) in the subject.

20. The system according to claim 17, wherein the optical generator is configured to generate the stimulating light in a pulsed regime having a pulsing frequency of about 60 Hz.

* * * * *